(12) United States Patent
Aoyama et al.

(10) Patent No.: US 9,959,648 B2
(45) Date of Patent: May 1, 2018

(54) MEDICAL IMAGE DISPLAY APPARATUS AND CONTROL METHOD THEREFOR

(71) Applicant: CANON KABUSHIKI KAISHA, Tokyo (JP)

(72) Inventors: Gakuto Aoyama, Kyoto (JP); Masahiro Yakami, Kyoto (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days. days.

(21) Appl. No.: 15/026,310

(22) PCT Filed: Nov. 14, 2014

(86) PCT No.: PCT/JP2014/080835
§ 371 (c)(1),
(2) Date: Mar. 31, 2016

(87) PCT Pub. No.: WO2015/080029
PCT Pub. Date: Jun. 4, 2015

(65) Prior Publication Data
US 2016/0247303 A1    Aug. 25, 2016

(30) Foreign Application Priority Data
Nov. 28, 2013 (JP) ................. 2013-246672

(51) Int. Cl.
*G06T 11/60* (2006.01)
*A61B 6/00* (2006.01)
(Continued)

(52) U.S. Cl.
CPC .............. *G06T 11/60* (2013.01); *A61B 6/463* (2013.01); *A61B 6/469* (2013.01); *G06F 19/321* (2013.01);
(Continued)

(58) Field of Classification Search
CPC .. G09G 2340/045; G09G 5/373; G09G 5/391; G09G 3/2044; G06T 2207/10081;
(Continued)

(56) References Cited

U.S. PATENT DOCUMENTS 7,250,988 B2    7/2007  Aoyama et al.
7,545,388 B2 *  6/2009  Wright .................. G06T 3/4007
                                                         345/606
(Continued)

FOREIGN PATENT DOCUMENTS

JP    2009-005906 A    1/2009

OTHER PUBLICATIONS

Basics of Digital Image Processing and Usage of PC Software for Clinical Research, the first edition, Medical-Tribune Corp., Apr. 5, 2013, Fig. 6.
(Continued)

*Primary Examiner* — Antonio A Caschera
(74) *Attorney, Agent, or Firm* — Fitzpatrick, Cella, Harper & Scinto (57) ABSTRACT

A medical image display apparatus which displays, in a display screen, a display image having undergone gray level transform of changing number of gray levels of a medical image, obtains a representative value of pixel values concerning a region of a block, in the medical image, which corresponds to each partial region in a region designated in the display image. The medical image display apparatus sets a specific region in the display screen so as to include the designated region, and superimposes/displays and arranges obtained representative values on the specific region in correspondence with the arrangement of the partial regions.

16 Claims, 7 Drawing Sheets

(51) Int. Cl.
  *G06T 7/00* (2017.01)
  *G06F 19/00* (2018.01)
  *G06T 3/40* (2006.01)
  *G09G 5/02* (2006.01)
  *G09G 5/373* (2006.01)
  *G09G 5/377* (2006.01)
  *A61B 5/055* (2006.01)
  *A61B 8/00* (2006.01)
  *A61B 5/00* (2006.01)

(52) U.S. Cl.
  CPC .............. *G06T 3/40* (2013.01); *G06T 7/0012* (2013.01); *G09G 5/026* (2013.01); *G09G 5/373* (2013.01); *G09G 5/377* (2013.01); *A61B 5/055* (2013.01); *A61B 5/743* (2013.01); *A61B 5/7425* (2013.01); *A61B 8/463* (2013.01); *A61B 8/469* (2013.01); *G06T 2207/10081* (2013.01); *G06T 2207/10088* (2013.01); *G06T 2207/20104* (2013.01); *G09G 2340/12* (2013.01); *G09G 2354/00* (2013.01); *G09G 2380/08* (2013.01)

(58) Field of Classification Search
  CPC . G06T 2207/10088; G06T 2207/20104; G06F 19/321; H04N 1/6058; H04N 1/393; H04N 1/3935
  See application file for complete search history.

(56) References Cited

U.S. PATENT DOCUMENTS

| | | |
|---|---|---|
| 7,746,413 B2 | 6/2010 | Aoyama et al. |
| 2002/0089514 A1* | 7/2002 | Kitahara ............... G06K 15/02 345/600 |
| 2010/0014729 A1* | 1/2010 | Choi ..................... G06T 5/50 382/131 |

OTHER PUBLICATIONS

Mar. 3, 2015 International Search Report in Internal Appln. No. PCT/JP2014/080835.

Impixelregion, MathWorks, http://www.mathworks.co.jp/jp/help/images/ref/impixelregion.html (2012).

* cited by examiner

MEDICAL IMAGE DISPLAY APPARATUS AND CONTROL METHOD THEREFOR

TECHNICAL FIELD

The present invention relates to a medical image display apparatus, a control method, and a program.

BACKGROUND ART

With recent advances in the digitization of medical data, various types of medical images are archived as digital images, and doctors have increasing chances of performing image diagnosis upon displaying digital images on displays. In general, medical images are stored in formats complying with DICOM (Digital Imaging and Communications in Medicine) international standards. Medical images include CT (Computed Tomography) images and MRI (Magnetic Resonance Imaging) images. Each type of image includes a large amount of three-dimensional image data constituted by many tomographic images. A medical image display apparatus is used to efficiently and meticulously observe such a large amount of image data.

A conventional medical image display apparatus has, as display functions for tomographic images, a function of moving a tomographic position, a function of enlarging/reducing an overall image, a function of translating a display position, a gray level transform function, and the like. In this case, the gray level transform function is a function of transforming each pixel value of a gray scale according to a predetermined rule. In general, a CT image is expressed by a 12-bit gray level (4,096 gray levels) HU (Hounsfield Unit) value per pixel, which is stored as a pixel value. When a doctor observes a CT image, a medical image display apparatus displays the CT image upon transforming the HU values into the number of gray levels suitable for display. In this transform, 12-bit gray level pixel values are transformed into 8-bit gray levels by using, for example, two gray level transform parameters, that is, WC (Window Center) and WW (Window Width), defined by DICOM standards. That is, the image (display image) having simultaneously undergone a change in the number of gray levels and a change in gray level distribution is displayed on a display. This makes it easy to see the difference in HU value (gray level difference) between a specific organ and a tissue. For an image other than a CT image (for example, an MRI image, PET image, or ultrasound image), gray level transform similar to that described above is performed to make it easy to see the differences between pixel values (gray level differences).

Figure 6:
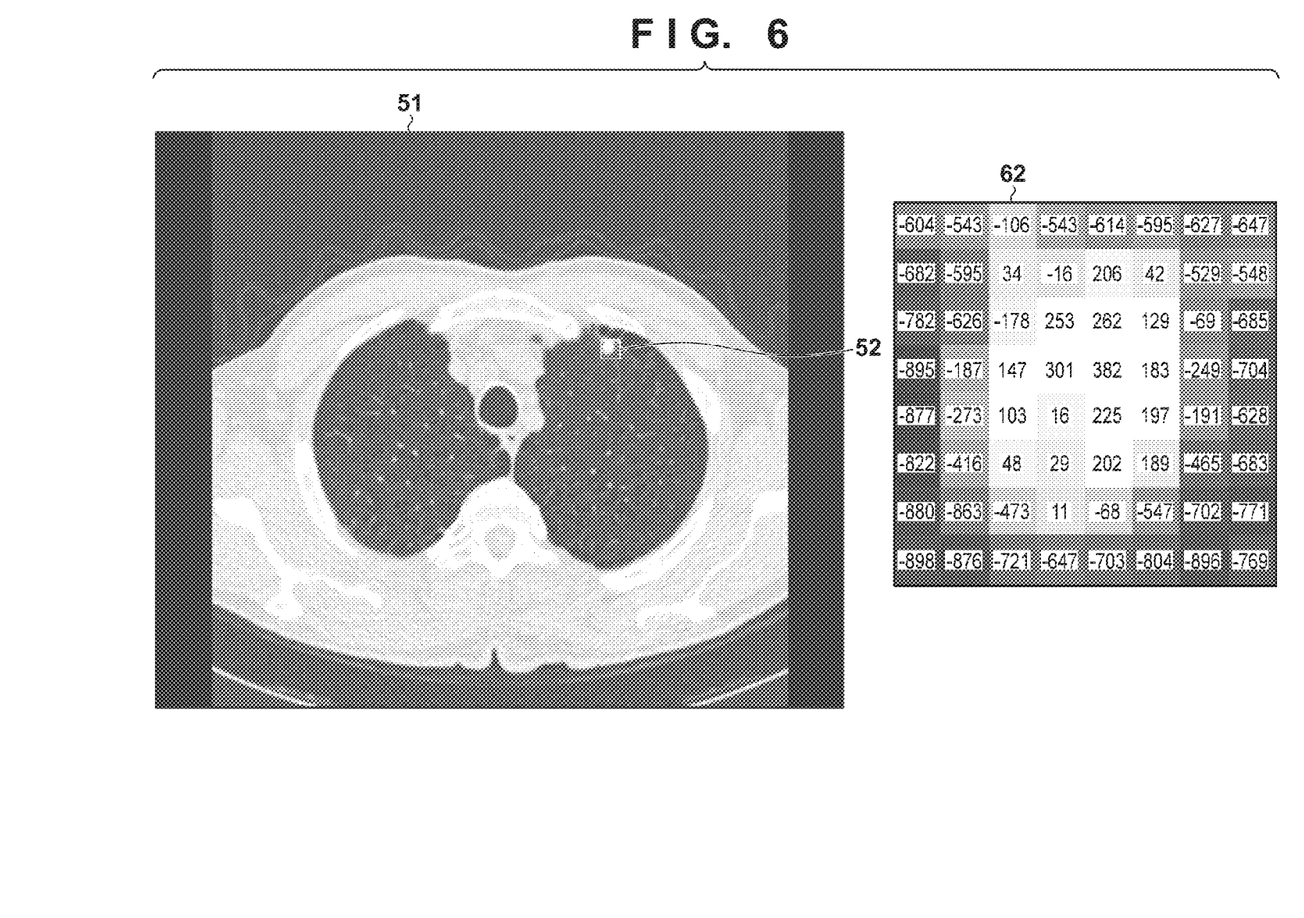
FIG. 6 is a view showing a frame display example using a pixel value display function.

Although the above gray level transform function makes it easy to see image gray level differences, this rather makes it difficult to see original pixel values (HU values of a CT image) (before changes in the number of gray levels and gray level distribution). For this reason, some computer software has a function of displaying the original pixel value of each pixel in numerical string. For example, as shown in FIG. 6, when the user designates a target region by drawing a rectangle (graphic 52), the software obtains an image in the target region, enlarges and displays the image in another window 62 at a high magnification, and displays the original pixel value (HU value) of each pixel on the enlarged image.

Figure 7:
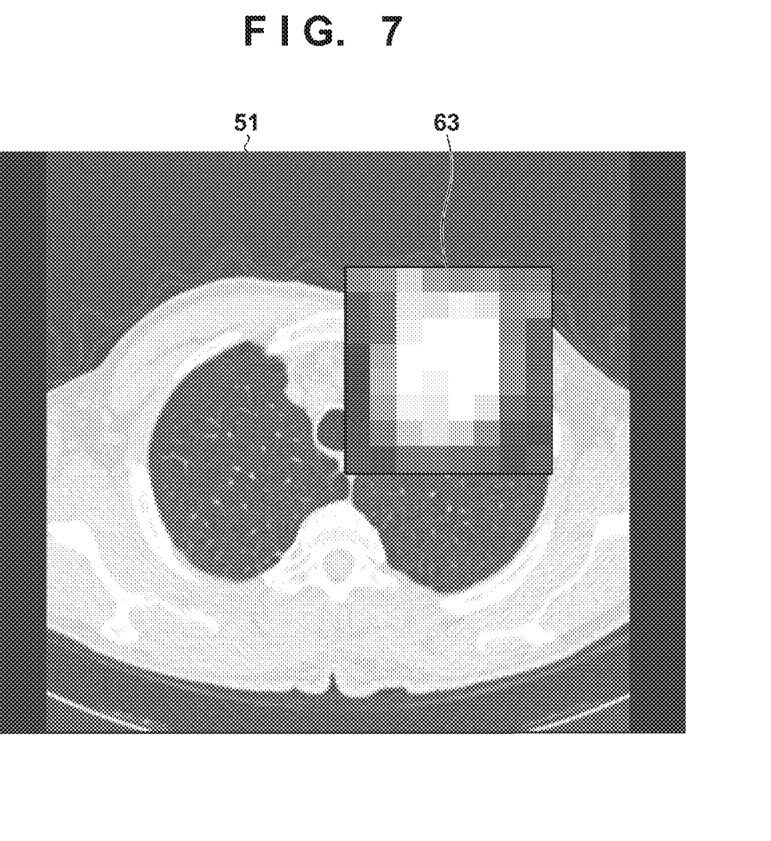
FIG. 7 is a view showing a frame display example using a loupe function.

Computer software used in general has an enlarged display function called loupe function for a frame in a rectangular region, as shown in FIG. 7. With the loupe function, when the user moves the cursor, the software generates a frame by enlarging a frame in a rectangular region with a predetermined size centered on the cursor position at a predetermined magnification, and displays the frame (graphic 63). In this case, the software displays the enlarged frame such that its center coincides with the cursor position (http://www.mathworks.co.jp/jp/help/images/ref/impixelregion.html).

When using a medical image display apparatus like that described above, there are demands to see a display image before enlargement, that is, an overall image, and simultaneously see an enlarged image in a target region and each pixel value in the target region. However, in the above pixel value display, since a display image and each pixel value are respectively displayed in windows at different positions, it is difficult for the user to simultaneously see them. On the other hand, when using the loupe function, although an enlarged frame is displayed at the cursor position, the frame before enlargement is hidden in the region where the enlarged frame is displayed. Even if, therefore, the pixel value display function is combined with the loupe function, the above problem cannot be solved.

SUMMARY OF INVENTION

An embodiment of the present invention is made in consideration of the above problem and provides a display function which makes it possible to simultaneously see a display image and each pixel value in a target region.

According to one aspect of the present invention, there is provided a medical image display apparatus which displays, in a display screen, a display image having undergone gray level transform that is changing number of gray levels of a medical image, the apparatus comprising: obtaining means for obtaining a representative value of pixel values concerning a region of a block, in the medical image, which corresponds to each partial region in a region designated in the display image; setting means for setting a specific region in the display screen so as to include the designated region; and display control means for superimposing/displaying and arranging representative values obtained by the obtaining means on the specific region in correspondence with an arrangement of the partial regions.

According to another aspect of the present invention, there is provided a method of controlling a medical image display apparatus which displays, in a display screen, a display image having undergone gray level transform of changing number of gray levels of a medical image, the method comprising: an obtaining step of obtaining a representative value of pixel values concerning a region of a block, in the medical image, which corresponds to each partial region in a region designated in the display image; a setting step of setting a specific region in the display screen so as to include the designated region; and a display control step of superimposing/displaying and arranging representative values obtained in the obtaining step on the specific region in correspondence with an arrangement of the partial regions.

Further features of the present invention will become apparent from the following description of exemplary embodiments (with reference to the attached drawings).

DESCRIPTION OF EMBODIMENTS

A preferred embodiment of the present invention will be described in detail below with reference to the accompanying drawings.

Figure 1:
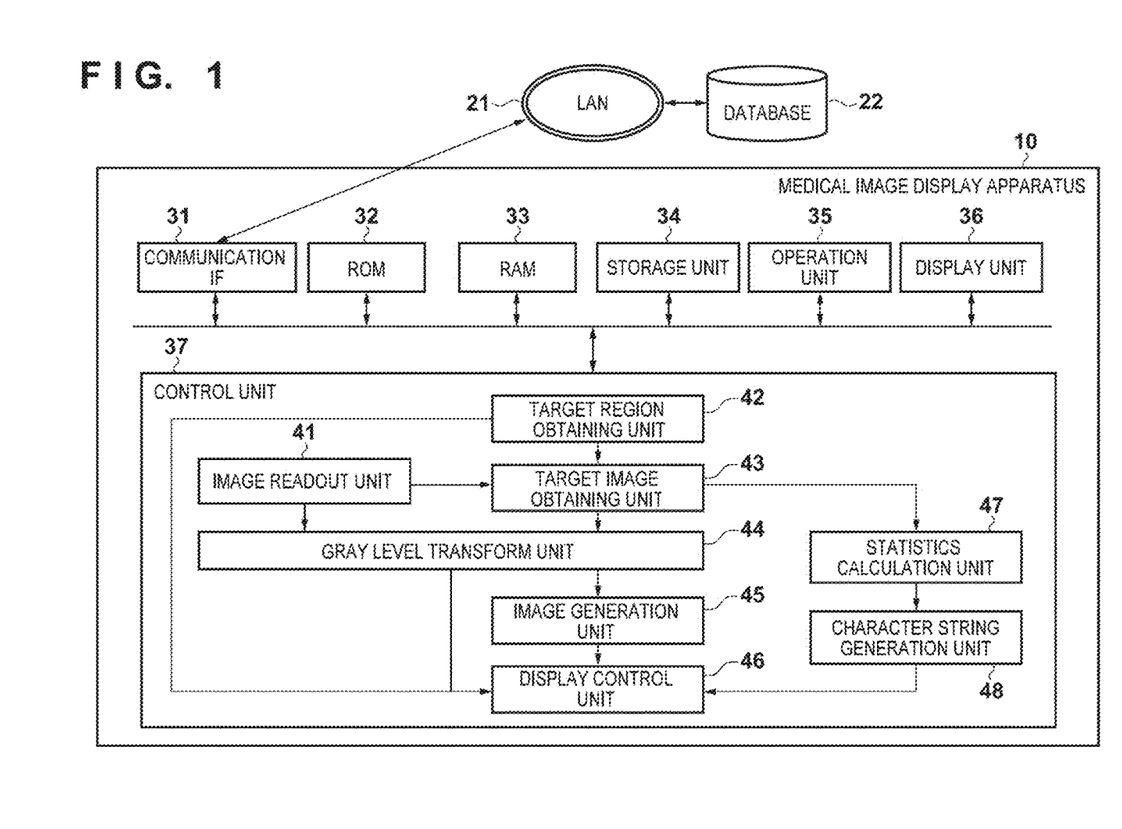
FIG. 1 is a block diagram showing an example of the overall arrangement of a medical image display system according to an embodiment.

FIG. 1 is a block diagram showing an example of the overall arrangement of a medical image display system including a medical image display apparatus according to an embodiment. The medical image display system includes a medical image display apparatus 10 and a database 22. These apparatuses are communicatively connected to each other via a communication means. In this embodiment, a LAN 21 (Local Area Network) is used as such a communication means. The database 22 manages and stores medical information such as medical images. The medical image display apparatus 10 obtains medical images managed by the database 22 via the LAN 21.

The composition of the medical image display apparatus 10 will be described as follows. The medical image display apparatus 10 includes a communication IF 31, a ROM 32, a RAM 33, a storage unit 34, an operation unit 35, a display unit 36, and a control unit 37. The communication IF (Interface) 31 is implemented by, for example, a LAN card or the like, and controls communication between an external apparatus (for example, the database 22) and the medical image display apparatus 10 via the LAN 21. The ROM (Read Only Memory) 32 is implemented by a nonvolatile memory or the like, and stores various types of programs and the like. The RAM (Random Access Memory) 33 is implemented by a volatile memory or the like, and temporarily stores various types of information. The storage unit 34 is implemented by, for example, an HDD (Hard Disk Drive) or the like, and stores various types of information. The operation unit 35 is implemented by, for example, a keyboard, a mouse, and the like, and inputs instructions from the user into the apparatus. The display unit 36 is implemented by, for example, a display or the like, and displays various types of information to the user (for example, a doctor).

The control unit 37 is implemented by, for example, a CPU (Central Processing Unit) or the like, and comprehensively controls processing in the medical image display apparatus 10. The control unit 37 is provided with, as its functional components, an image readout unit 41, a target region obtaining unit 42, a target image obtaining unit 43, a gray level transform unit 44, an image generation unit 45, a display control unit 46, a statistics calculation unit 47, and a character string generation unit 48. These components can be implemented by making a CPU (not shown) read out programs stored in the ROM 32, the storage unit 34 or the like using the RAM 33 as a work area and execute the programs. Note that some or all of these components may be implemented by dedicated circuit(s) and the like.

The image readout unit 41 reads out a medical image (first image) from the database 22 via the communication IF 31 and the LAN 21. For the sake of easy understanding, the following description will exemplify a medical image complying with DICOM standards. However, the present invention can be easily applied to other types of images. In addition, the following will exemplify a case in which one medical image is displayed. Obviously, however, the present invention can be easily applied to a case in which a three-dimensional medical image constituted by many tomographic images like a CT image or MRI image is displayed. When, for example, applying the present invention to a three-dimensional medical image, an arbitrary tomographic image in a three-dimensional medical image is displayed in a predetermined region on the screen of the display unit 36. Processing in this embodiment may then be applied to the displayed tomographic image. Note that the tomographic image to be displayed on the screen of the display unit 36 can be arbitrarily changed in accordance with an instruction from the user.

The gray level transform unit 44 performs gray level transform (including a change in the number of gray levels and a change in gray level distribution) of images (first and second images) based on the WC and WW values defined in DICOM standards. Note that the second image will be described later. Since WC and WW values are written in the header portion of a DICOM image, the gray level transform unit 44 can perform gray level transform by using the WC and WW values written in the header portion. Note that a GUI (Graphical User Interface) for changing WC and WW values may be displayed on the display unit 36 to make it possible to change the WC and WW values in accordance with a user input inputted from the operation unit 35. The gray level transform unit 44 can perform gray level transform desired by the user by performing gray level transform using the WC and WW values changed via the GUI. In general, a CT image is expressed by a 12-bit gray level (4,096 gray levels) HU (Hounsfield Unit) value per pixel, which is stored as a pixel value. The gray level transform unit 44 performs gray level transform by using WC and WW values to convert each 12-bit gray level pixel value into an 8-bit gray level (256 gray levels), thereby obtaining a display image to be displayed on the display unit 36. Note that when the display unit 36 is configured to directly display an image before gray level transform, the gray level transform unit 44 may be omitted.

The display control unit 46 displays the first image (display image) after gray level transform by the gray level transform unit 44 in a predetermined region (a window in the GUI) on the screen of the display unit 36. In addition, the display control unit 46 displays a graphic indicating the target region obtained by the target region obtaining unit 42 (to be described later) on the screen of the display unit 36. Furthermore, the display control unit 46 has a function of superimposing/displaying a second image (to be described later) on a display image and a function of superimposing/displaying arbitrary character strings on an arbitrary image. The display control unit 46 can also translate the display position (X- and Y-coordinates) of a display image and change a display size (enlargement ratio) in accordance with instructions from the user. In synchronism with such translation of the display position and change in display size, the display control unit 46 translates information (graphic or character strings) superimposed on a displayed image or change the display size. Even when information is translated or a display size is changed, the relative positional relationship between the display image and the image (information) superimposed/displayed on it is maintained.

The target region obtaining unit 42 obtains information indicating an arbitrary position (the position designated by the user) on the first image (that is, the display image) after gray level transform displayed on the display unit 36 in accordance with a user input inputted from the operation unit 35. In the medical image display apparatus according to this embodiment, user input can be implemented by, for example, operating the pointing device (for example, the mouse) of the operation unit 35. Position information on an image which is designated by the pointing device is calculated from an image display position on the screen of the display unit 36 and a cursor position corresponding to the operation of the pointing device. The target region obtaining unit 42 obtains, as a target region, a rectangular region with a predetermined size centered on the position designated by the pointing device.

The target image obtaining unit 43 obtains, as a target image, an image corresponding to the target region, in the first image read out by the image readout unit 41, which is designated by the target region obtaining unit 42. Assume that the target region can be divided into blocks (partial regions) each having a predetermined size. This embodiment will exemplify a case in which each partial region in a target region is formed from one pixel. In this case, the representative value of each block (each pixel) of the target image obtained from the first image is exactly the pixel value of one pixel in the block. Note that a partial region (block) is constituted by a predetermined number of adjacent pixels, for example, a total of four pixels of 2 pixels (vertical)×2 pixels (horizontal), it is possible to use the value (for example, the statistic) calculated from the four pixels constituting the block as the representative value of a block of the target image. For example, the value to be calculated as a representative value includes the average value or median value of four pixel values. It is also possible to allow the user to set the size of such a partial region as "m×n pixels" (where m and n are natural numbers) using, for example, the operation unit 35.

The image generation unit 45 generates an enlarged image by enlarging a target image at predetermined magnifications (enlargement ratios) in the vertical and horizontal directions. In this case, the enlargement ratios in the horizontal and vertical directions may be the same or different values. Alternatively, the user may be allowed to change the respective enlargement ratios in the vertical and horizontal directions via a GUI. Furthermore, the image generation unit 45 replaces the color of part of the enlarged image (a portion determined in accordance with a predetermined rule) with a transparent color (a background transparent portion). A description will be made later about which portion of the enlarged image is to have a transparent color. With the above processing, the image generation unit 45 generates the second image. That is, the second image is the image obtained by replacing the color of part of the enlarged image generated by enlarging the target image with a transparent color. When the second image is superimposed/displayed on the first image, the first image can be seen through the transparent portion of the first image. Alternatively, the image generation unit 45 may generate the second image by making the overall enlarged image translucent by setting a predetermined transmittance for the overall enlarged image. Note that a technique of making a portion or all of an image transparent or translucent is generally known as an image display technique using an plane (information for designating a transmittance for the image for each pixel position).

The statistics calculation unit 47 calculate the statistics (for example, the average, variance, maximum value, and minimum value) of the pixel values of all the pixels of the target image obtained by the target image obtaining unit 43.

The character string generation unit 48 obtains the representative value (a pixel value in this embodiment) of each block of the target image obtained by the target image obtaining unit 43 and the statistics calculated by the statistics calculation unit 47 (numerical values obtaining function). The character string generation unit 48 generates character strings expressing these numerical value data in numerals (character string generation function). The character string generation unit 48 also decides a display form (for example, a display color, line width, and ornamental writing) for each character string corresponding to each pixel value based on each pixel value of the target image (in accordance with a predetermined rule) (display form changing function). Note that a specific example of a method of deciding a display form will be described later.

Next, an example of a processing procedure in the medical image display apparatus 10 shown in FIG. 1 will be described as follows with reference to FIGS. 2 to 5.

Figure 2:
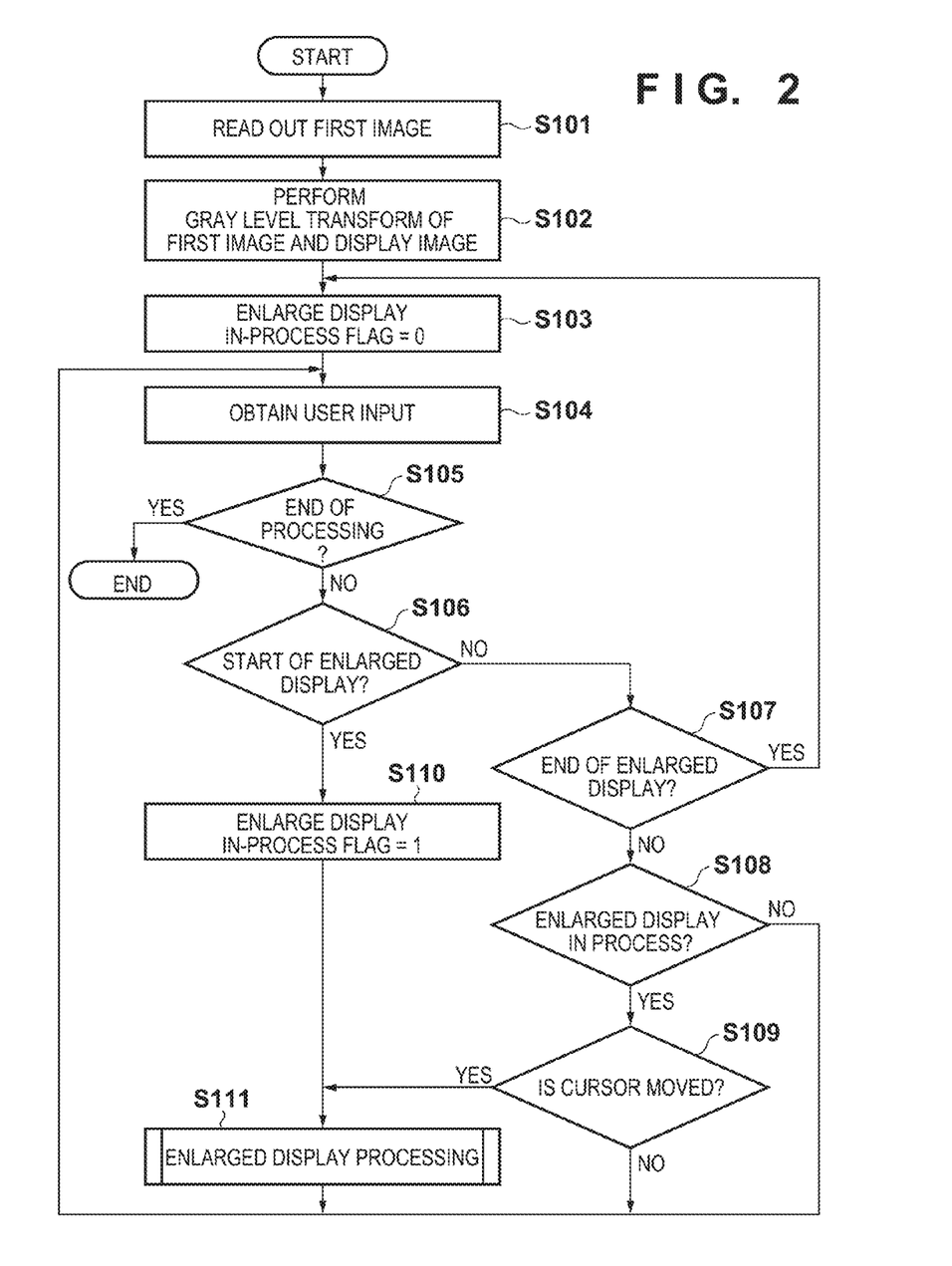
FIG. 2 is a flowchart showing an example of image display processing by the medical image display apparatus.
Figure 4:
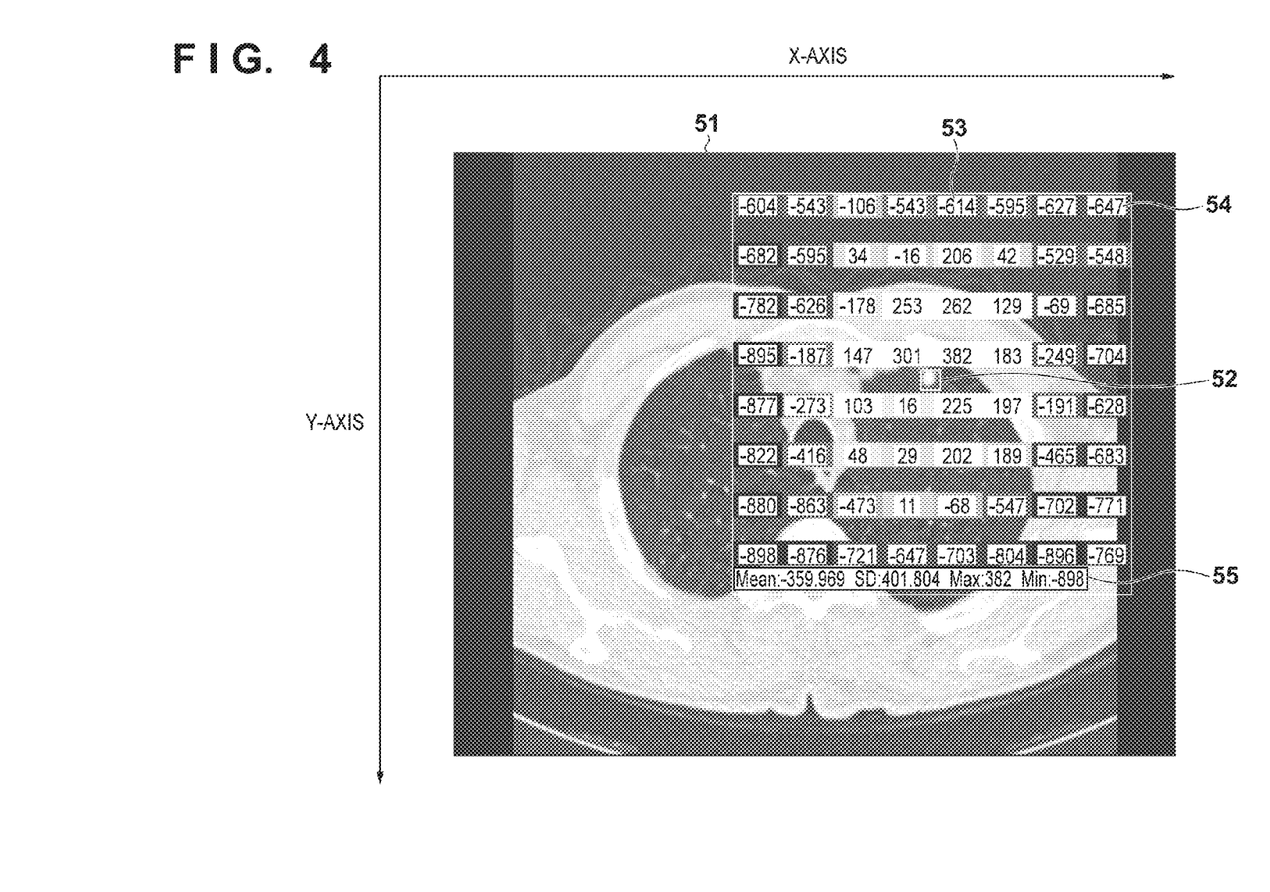
FIG. 4 is a view showing an example of a frame displayed on a display unit.
Figure 5:
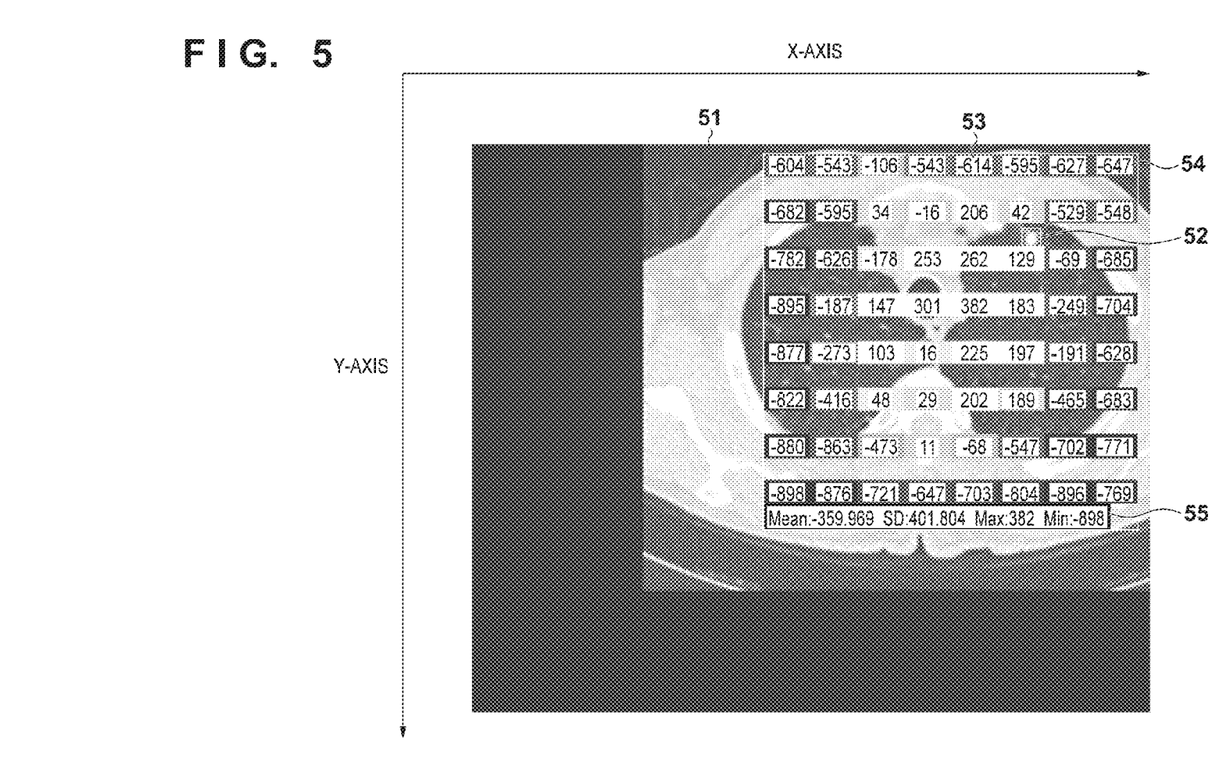
FIG. 5 is a view showing an example of a frame displayed on the display unit.

FIG. 2 is a flowchart showing an example of a procedure for image display processing in the medical image display apparatus 10. FIGS. 4 and 5 are respectively the first and second examples of screens displayed on the display unit 36. Referring to FIGS. 4 and 5, as indicated by them, the X-axis is taken in the right direction, and the Y-axis in the down direction.

When the user issues an instruction to read out the first image via the operation unit 35, the processing shown in FIG. 2 starts. In step S101, the image readout unit 41 of the medical image display apparatus 10 reads out the first image (medical image) from the database 22 via the communication IF 31 and the LAN 21, and stores the image in the RAM 33. In step S102, the gray level transform unit 44 reads out the first image from the RAM 33, and generates a display image (the first image after gray level transform) by performing gray level transform with respect to the first image. The display control unit 46 then displays the display image in a predetermined display region (a window 51 in FIG. 4) on the screen of the display unit 36 (step S102). In step S103, the control unit 37 substitutes 0 (a value indicating that enlarged display is not being performed) into an enlarged display in-process flag, and stores it in the RAM 33.

When a user input is obtained from the operation unit 35 in step S104, the control unit 37 determines in step S105 whether the obtained user input is a processing end command. If the user input is a processing end command (YES in step S105), the processing in FIG. 2 is terminated. If the user input is not a processing end command (NO in step S105), the process advances to step S106, in which the control unit 37 determines whether the user input is an enlarged display start command. If the user input is an enlarged display start command (YES in step S106), the process advances to step S110. If the user input is not an enlarged display start command (NO in step S106), the process advances to step S107.

In step S107, the control unit 37 determines whether the user input is an enlarged display end command. If the user input is an enlarged display end command (YES in step S107), the process returns to step S103. If the user input is not an enlarged display end command (NO in step S107), the process advances to step S108. In step S108, the control unit 37 reads out the enlarged display in-process flag from the RAM 33 to determine whether the flag is 1 or 0, that is, whether the enlarged display is in process. If the user input is an enlarged display in-process flag (YES in step S108), the process advances to step S109. If the user input is not an enlarged display in-process flag (NO in step S108), the process returns to step S104. In step S109, the control unit 37 determines whether the user input is a cursor movement command. If the user input is a cursor movement command (YES in step S109), the process advances to step S111. If the user input is not a cursor movement command (NO in step S109), the process returns to step S104.

In step S110, the control unit 37 substitutes 1 (a value indicating that enlarged display is being performed) into the enlarged display in-process flag, and stores it in the RAM 33. In step S111, the medical image display apparatus 10 performs enlarged display processing. The enlarged display processing in step S111 will be described in detail with reference to FIG. 3.

Figure 3:
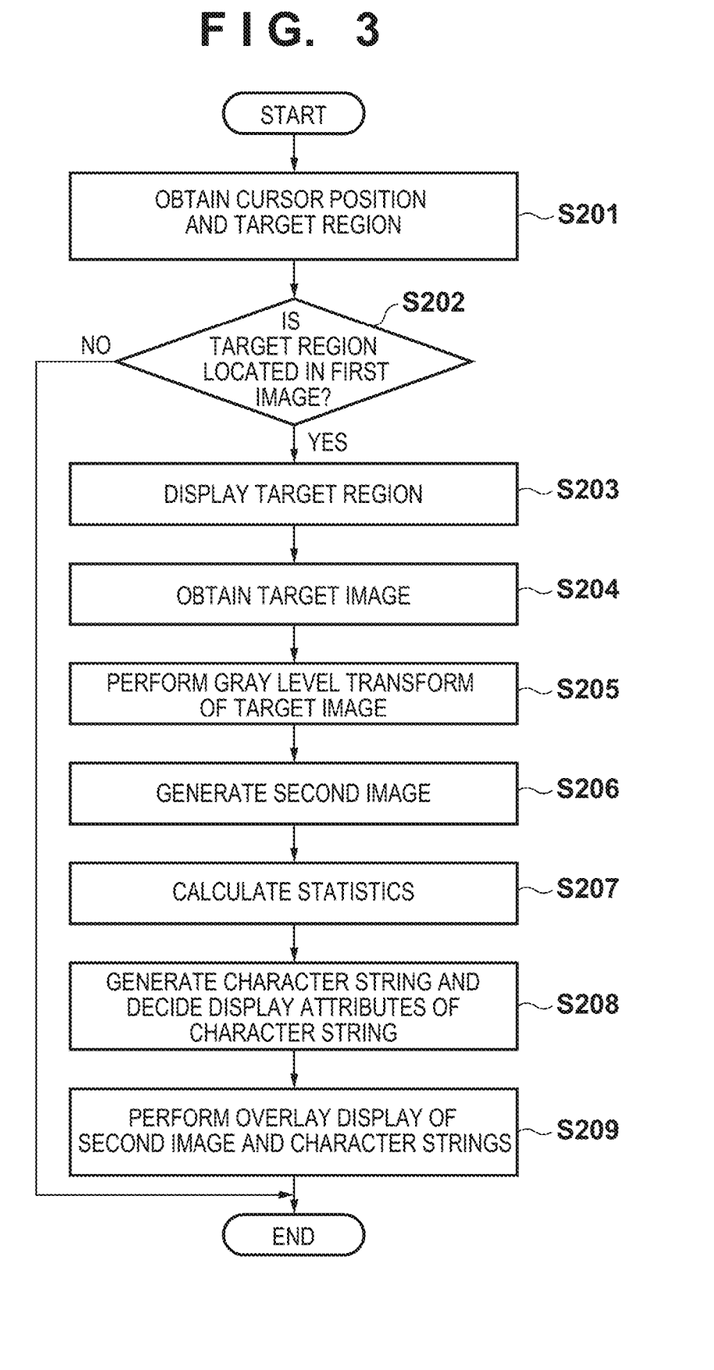
FIG. 3 is a flowchart showing an example of enlarged display processing by the medical image display apparatus.

FIG. 3 is a flowchart showing an example of a procedure for enlarged display processing (step S111 in FIG. 2) in the medical image display apparatus 10. In step S201, the target region obtaining unit 42 obtains a target region on the first image in the following procedure. First of all, the target region obtaining unit 42 obtains a cursor position $P_0(x_0, y_0)$ on the screen of the display unit 36 and a display region $R_1\{(x_{s1}, y_{s1}), (x_{e1}, y_{e1})\}$ (the window 51 in FIG. 4). In this case, $x_0$ and $y_0$ respectively represent the X- and Y-coordinates of the cursor position $P_0$, and $(x_{s1}, y_{s1})$ and $(x_{e1}, y_{e1})$ respectively represent the X- and Y-coordinates of an upper left position and lower right position in the display region $R_1$ of the image in the order named.

The target region obtaining unit 42 then obtains a target region $R_2\{(x_{s2}, y_{s2}), (x_{e2}, y_{e2})\}$ (a graphic 52 in FIG. 4) having a target region size (w, h) centered on the cursor position $P_0(x_0, y_0)$ according to equations (1) to (4) given below. In this case, $(x_{s2}, y_{s2})$ and $(x_{e2}, y_{e2})$ respectively represent the X- and Y-coordinates of an upper left position and lower right position in the display region $R_2$ in the order named. Note that in the case shown in FIG. 4, the target region has a target region size (8, 8) of 8 pixels in each of the vertical and horizontal directions.

$$x_{s2} = x_0 - w/2 \quad (1)$$

$$y_{s2} = y_0 - h/2 \quad (2)$$

$$x_{e2} = x_0 + w/2 \quad (3)$$

$$y_{e2} = y_0 + h/2 \quad (4)$$

In step S202, the target region obtaining unit 42 determines whether the target region $R_2\{(x_{s2}, y_{s2}), (x_{es}, y_{e2})\}$ exists in the display region $R_1\{(x_{s1}, y_{s1}), (x_{e1}, y_{e1})\}$ of the first image (display image) (step S202). If the target region $R_2$ exists in the display region $R_1$ (YES in step S202), the process advances to step S203. Otherwise (NO in step S202), the processing in FIG. 3 is terminated. Note that it is possible to determine whether the target region $R_2$ exists in the display region $R_1$ according to, for example, equations (5) to (8) given below. That is, if all equations (5) to (8) are met, the target region $R_2\{(x_{s2}, y_{s2}), (x_{es}, y_{e2})\}$ exists in the display region $R_1\{(x_{s1}, y_{s1}), (x_{e1}, y_{e1})\}$ of the first image.

$$x_{s1} \leq x_{s2} \quad (5)$$

$$y_{s1} \leq y_{s2} \quad (6)$$

$$x_{e1} \geq x_{e2} \quad (7)$$

$$y_{e1} \geq y_{e2} \quad (8)$$

In step S203, the display control unit 46 displays a graphic (the graphic 52 in FIG. 4) indicating the target region $R_2\{(x_{s2}, y_{s2}), (x_{es}, y_{e2})\}$ on the first image. In step S204, the target image obtaining unit 43 reads out a portion (target image), of the first image before gray level transform, which corresponds to the target region $R_2\{(x_{s2}, y_{s2}), (x_{es}, y_{e2})\}$ from the RAM 33. In step S205, the gray level transform unit 44 executes gray level transform with respect to the target image read out in step S204. Note that if a partial region of the target region is constituted by a plurality of pixels (for example, 2×2 pixels), the target image is also constituted by the representative values of the respective blocks, and the gray level transform unit 44 executes gray level transform concerning the representative values.

In step S206, the image generation unit 45 generates an enlarged image by enlarging the target image after the gray level transform by the gray level transform unit 44 at predetermined enlargement ratios in the vertical and horizontal directions. In the case shown in FIG. 4, the same enlargement ratio (a magnification of m) is set in the vertical and horizontal direction. The image generation unit 45 further sets a transparent color for part of the enlarged image so as to make it possible to see through the background (step S206). In this embodiment, the image generation unit 45 sets a transparent color for a lower half region (m pixels (horizontal)×m/2 pixels (vertical)) of an enlarged block (a region of m pixels (horizontal)×m pixels (vertical) as a partial region of the enlarged image which corresponds to one block (one pixel in this embodiment) of the target image. Setting the lower half region of each enlarged block to a transparent region in this manner will generate an enlarged image (second image) including slit-like background transparent portions in the horizontal direction, which is displayed as an image 53 (FIG. 4).

According to the above description, the lower half region of an enlarged block is set to a transparent region so as to form a slit grating in the horizontal direction as a whole. However, the upper half region may be set to a transparent region instead of the lower half region. Another example is that the second image including slit-like background transparent portions in the vertical direction is generated by setting the right half region or left half region (m/2 pixels (horizontal)×m pixels (vertical)) of each enlarged block (m pixels (horizontal)×m pixels (vertical)) to a transparent region upon setting a transparent color for it. That is, an enlarged image (second image) having a slit grating formed in the vertical direction as a whole is generated.

Still another example is that a second image including background transparent portions in a checkered pattern is generated by alternately setting a transparent color for upper and lower half portions (or right and left half portions) in accordance with pixel positions. In the above example, a transparent color is set for the upper, lower, right, or left half region of each enlarged block. However, the present invention is not limited to this. A transparent color may be set for a region larger or smaller than a half region. Furthermore, a transparent color setting is not limited to a transparent state and may be made to have a predetermined transparency degree. Alternatively, the image generation unit 45 may set a predetermined transmittance (for example, a transmittance of 50%) for the overall second image to make the overall second image translucent.

In step S207, the statistics calculation unit 47 calculates the statistics of the pixel values of the target image obtained by the target image obtaining unit 43 in step S204. In this embodiment, the target image obtaining unit 43 calculates, as the statistics, for example, the average, variance, maximum value, and minimum value of the pixel values in the target image. In step S208, the character string generation unit 48 then generates character strings expressing the respective representative values (pixel values in this case) of the target image (step S204) obtained by the target image obtaining unit 43 and the statistics (step S207) calculated by the statistics calculation unit 47 in numerals. For example, in the case of a CT image, representative values (pixel values) are HU values. In the case shown in FIG. 4, the respective pixel values of the target image is displayed as a character string 54, and the statistics of the pixel values of the target image is displayed as a character string 55. Note that the character string 55 representing the statistics calculated in step S207 may be displayed outside the image 53. This is because the statistics calculated in step S207 are numerical values concerning the overall target region, but are not numerical values corresponding to each partial region (a one-pixel region in this embodiment).

In addition, the character string generation unit 48 decides the display attributes (for example, a display form including a display color) of each character string corresponding to each pixel value based on each pixel value (the display color of a non-transparent region in each enlarged block of the second image) of the enlarged image after gray level transform (step S208). In the case shown in FIG. 4, the character color is set to white when the display density of the enlarged image after gray level transform is less than a predetermined threshold (when the display color is near black), while the character color is set to black when the display density is equal to or more than the threshold (when the display color is near white). A method of deciding a display form for characters may include, for example, changing the character color to a color other than white and black, changing the font type of characters, and changing the typeface to boldface or lightface or to italic or non-italic. In addition, it is possible to display a frame border surrounding a character and decide the display form (color, line type, and the like) of this frame border. Although the above description has exemplified the arrangement in which the character string generation unit 48 decides the display form of a character. However, the present invention is not limited to this. For example, the same display form may be set in advance for all characters in the character string generation unit 48, and the display control unit 46 may change the display form of a character by the same method as described above.

In step S209, the display control unit 46 then superimposes/displays the second image and the character stings on the display unit 36. In this case, the display control unit 46 displays the second image (the image 53 in FIG. 4) at a position (nearly the center of the target region) where the center of the second image almost coincides with the center of the graphic (the graphic 52 in FIG. 4) indicating the target region. If, however, as in the case exemplified by FIG. 4, when the transparent region of the second image is located at a position slightly shifted from the center of the second image, the display position is slightly shifted so as to locate a graphic indicating a target region in the transparent region of the second image. For example, in the case shown in FIG. 4, the second image is displayed at a position shifted upward by four pixels so as to locate the graphic 52 indicating the target region (8×8 pixel region) in the transparent region of the second image. Furthermore, the display control unit 46 superimposes/displays the character strings generated in step S208 on the non-transparent portion of the partial region of the second image. That is, the character strings are displayed to coincide with the opaque portion (non-transparent region) of the enlarged block (the m×m pixel region in the above case) corresponding to the partial region of the target region of the second image. In this case, if the character strings are longer than the opaque portion of the enlarged block of the second image, the font size of the character strings is reduced to make the character strings fall within the opaque portion of the enlarged block of the second image.

FIG. 5 shows the second example of the screen displayed on the display unit 36. In the case shown in FIG. 5, the second image (the image 53 in FIG. 5) is displayed at a position where the center of the second image is shifted from nearly the center of the graphic (the graphic 52 in FIG. 5) indicating the target region. If, for example, the graphic 52 indicating the target region is located near the boundary of a display region (not show) of the image determined by the display control unit 46, the display control unit 46 adjusts the display position of the image 53. For example, when the image 53 is displayed at a position where its center coincides with nearly the center of the graphic 52, part of the image 53 sometimes protrudes from the display region (the window 51) of the image. In such a case, the display control unit 46 performs the processing of shifting the display position to make the image 53 fall within the display region. Note that this processing is an option so that even if part of the image 53 protrudes from the window 51, the graphic 52 indicating the target region may be displayed at nearly the center of the image 53.

The above processing provides the effect of allowing the user to simultaneously see the first image (display image) after gray level transform, the graphic indicating the target region, the second image (enlarged image), and the character strings representing the respective pixel values of the first image before the gray level transform.

(First Modification)

Note that in the above embodiment, the character string generation unit 48 decides the display attributes of each character string corresponding to each pixel value based on each pixel value of the enlarged image after gray level transform (the display color of the non-transparent region of the second image) (step S208). However, the present invention is not limited to this. The display attributes (for example, the display color) of each character string corresponding to each pixel value may be decided based on each pixel value (or each representative value) of the target image obtained from the first image. For example, pixel values (representative values) are classified into a plurality of groups according to predetermined pixel value (representative value) ranges, and the correspondence relationship between each group and a character display form is determined in advance. It is then possible to determine to which group each pixel value (representative value) of the target image obtained from the first image belongs and to decide the display form of each character string from the correspondence relationship between the group and the display form.

It is preferable to determine in advance pixel value ranges for grouping in consideration of medical or clinical meanings. For example, it is clinically known that the pixel values of a CT image indicate HU values, and HU value ranges are approximately determined for the respective components in the body as described below. It is therefore preferable to determine the display colors of characters for the respective HU value ranges. Note that pixel value ranges may be set for HU value ranges which are not described below so as to make each HU value range fall within either range described below, thereby deciding the correspondence relationship between all the pixel values and the display forms (display colors) of characters. This allows the user to easily understand, from the display color of a character string indicating each pixel value (representative value) displayed on the second image, what components included in the target region.

| Components in Body | HU Value as a reference (Approximate values) |
|---|---|
| Metal | Several Thousands |
| Bone | Several Hundreds to 1000 |
| Soft Tissue | 17 to 80 |
| Water | 0 to 16 |
| Fat | −1 to −128 |
| Air | −1000 |

According to the above description, the character string generation unit 48 is configured to change a display form. However, the character string generation unit 48 may set the same display form for all characters, and the display control unit 46 may change the display form of a character by the same method as described above.

(Second Modification)

In addition, it is possible to switch between the method of displaying the second image and the method of displaying character strings to be superimposed/displayed to show representative values in accordance with a user instruction. For example, in user input obtaining processing (step S104) shown in FIG. 2, a user instruction for switching between the method of displaying the second image and the method of displaying character strings to be superimposed is obtained (display changing instruction). In enlarged display processing (step S111), the processing performed by the image generation unit 45 and/or the display control unit 46 is partially changed as follows in accordance with a display changing instruction. The following exemplifies three types of display changing instructions.

The first display changing instruction is used to instruct whether to set a transparent color to part of an enlarged image in the generation of the second image by the image generation unit 45 (step S206). The second display changing instruction is used to instruct whether to superimpose/display the second image and character strings on the first image or display a display window different from the first image in superimposed display of the second image and the character strings by the display control unit 46 (step S209). The third display changing instruction is used to instruct to inhibit from displaying the second image or character strings in superimposed display of the second image and character strings by the display control unit 46 (step S209).

Assume that an instruction is issued to inhibit from setting a transparent color to part of an enlarged image in accordance with the first display changing instruction and display the second image and character strings in a display window different from the first image (display image) after gray level transform in accordance with the second display changing instruction. In this case, the display screen exemplified in FIG. 6 is obtained. That is, the second image (without any transparent region) is displayed in the window 62 different from the window 51, together with character strings indicating the representative values of the respective partial regions. In this case, since there is no transparent region, the character strings may be located at any positions in the enlarged blocks. In the case in FIG. 6, a character string is arranged in the center of each enlarged block. Note that FIG. 6 shows the respective character strings as black characters on the white background. However, the present invention is not limited to this. For example, as exemplified by FIGS. 4 and 5, if a display density is less than a predetermined threshold (if a display color is near black), characters may be displayed in a white character color, whereas if a display density is equal to or more than the threshold (if a display color is near white), characters may be displayed in a black character color.

Assume that an instruction is issued to inhibit from setting a transparent color to part of an enlarged image in accordance with the first display changing instruction and inhibit from superimposing/displaying character strings in accordance with the third display changing instruction. In this case, the display screen exemplified by FIG. 7 is obtained. That is, although the second image is displayed in an enlarged frame 63, no transparent region exists, and no character strings indicating representative values are displayed.

In addition, if an instruction is issued to inhibit from displaying the second image in accordance with the third display changing instruction, only character strings indicating representative values are displayed in a specific region (the region in which the image 53 is displayed in FIG. 4) in a display image. In this case, since the representative values are arranged at display positions like those shown in FIG. 4, the representative values arranged in correspondence with the respective positions of the partial regions are superimposed/displayed in a specific region corresponding to the display region of the second image.

It is possible to implement both the display method characteristic to the present invention and the method as in the related art by switching the display methods in accordance with display changing instructions as described above.

The above embodiment is a typical embodiment of the present invention. However, the present invention is not limited to the embodiment described above with reference to the accompanying drawings and can be modified as needed within the range in which the spirit of the present invention is not changed.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-246672, filed Nov. 28, 2013 which is hereby incorporated by reference herein in its entirety.

The invention claimed is:

1. A medical image display apparatus that displays, on a display screen, a display image having undergone gray level transform of changing a number of gray levels of a medical image, the medical image display apparatus comprising:
at least one processor and at least one memory that cooperate to act as units comprising:
(a) an obtaining unit configured to obtain, in the medical image, a representative value of pixel values concerning a region of a block, wherein (1) the block corresponds to a partial region in a region designated in the display image and (2) each partial region in the designated region corresponds to a respective block;
(b) a setting unit configured to set a specific region in the display screen so as to include the designated region; and
(c) a display control unit configured to (i) superimpose and display and (ii) arrange representative values obtained by the obtaining unit on the specific region in correspondence with an arrangement of the partial regions.

2. The medical image display apparatus according to claim 1, wherein the display control unit displays the representative value in a display form corresponding to the representative value when superimposing and displaying the representative value.

3. The medical image display apparatus according to claim 2, wherein the display control unit changes the display form of the representative value in accordance with a value obtained by processing the representative value by the gray level transform.

4. The medical image display apparatus according to claim 2, wherein the display control unit classifies representative values into a plurality of groups and changes a display form of a representative value in accordance with a group to which the representative value belongs.

5. The medical image display apparatus according to claim 4, wherein the plurality of groups comprise ranges of values classified in correspondence with components in a body.

6. The medical image display apparatus according to claim 2, wherein a display form of the representative value is changed by changing a display form of a character string indicating the representative value.

7. The medical image display apparatus according to claim 2, wherein a display form of the representative value is changed by changing a display form of a frame border surrounding the character string indicating the representative value.

8. The medical image display apparatus according to claim 1, further comprising a generation unit configured to generate an enlarged image of the designated region,
wherein the display control unit superimposes/displays the enlarged image on the specific region at a predetermined transmittance.

9. The medical image display apparatus according to claim 1, wherein the at least one processor and the at least one memory further cooperate to act as units comprising:
a generation unit configured to generate an enlarged image of a region, of the medical image, that corresponds to the designated region,
wherein the generation unit forms a portion of each of enlarged blocks corresponding to the blocks of the medical image in the enlarged image into a transparent portion, and
wherein the display control unit superimposes and displays the enlarged image on the specific region and superimposes and displays the representative value on a non-transparent region of each of the enlarged blocks.

10. The medical image display apparatus according to claim 9, wherein the generation unit generates the enlarged image with a slit grating being formed in a lateral direction by forming one of lower and upper regions of the enlarged block into a transparent region.

11. The medical image display apparatus according to claim 9, wherein the generation unit generates the enlarged image with a slit grating being formed in a vertical direction by forming one of right and left regions of the enlarged block into a transparent region.

12. The medical image display apparatus according to claim 9, wherein the setting unit sets a position of the specific region so as to locate the designated region in a transparent region formed in the enlarged image.

13. The medical image display apparatus according to claim 1, wherein the partial region and the block each comprise a one-pixel region, and
wherein the obtaining unit obtains a pixel value of a pixel of the block in the medical image as the representative value.

14. The medical image display apparatus according to claim 1, wherein the partial region and the block each comprise a region comprising a plurality of pixels, and
wherein the obtaining unit obtains statistic(s) of a plurality of pixel values of the block of the medical image as the representative value(s).

15. A method of controlling a medical image display apparatus that displays, on a display screen, a display image having undergone gray level transform of changing a number of gray levels of a medical image, the method comprising:
an obtaining step of obtaining, in the medical image, a representative value of pixel values concerning a region of a block, wherein (1) the block corresponds to a partial region in a region designated in the display image and (2) each partial region in the designated region corresponds to a respective block;
a setting step of setting a specific region in the display screen so as to include the designated region; and
a display control step of (i) superimposing and displaying and (ii) arranging representative values obtained in the obtaining step on the specific region in correspondence with an arrangement of the partial regions.

16. A non-transitory computer readable storage medium storing a program for causing a computer to execute a method of controlling a medical image display apparatus that displays, on a display screen, a display image having undergone gray level transform of changing a number of gray levels of a medical image, the method comprising:
an obtaining step of obtaining, in the medical image, a representative value of pixel values concerning a region of a block, wherein (1) the block corresponds to a partial region in a region designated in the display image and (2) each partial region in the designated region corresponds to a respective block;

a setting step of setting a specific region in the display screen so as to include the designated region; and a display control step of (i) superimposing and displaying and (ii) arranging representative values obtained in the obtaining step on the specific region in correspondence with an arrangement of the partial regions.

* * * * *